United States Patent [19]
Gillard et al.

[11] Patent Number: 5,563,417
[45] Date of Patent: Oct. 8, 1996

[54] PROCESS AND APPARATUS FOR AUTOMATICALLY CHARACTERISING, OPTIMISING AND CHECKING A CRACK DETECTION ANALYSIS METHOD

[75] Inventors: Hervé P. R. Gillard, Viry Chatillon; Véronique H. M. P. Prejean Lefevre, Sceaux, both of France

[73] Assignee: Societe Nationale d'Etude et de Construction de Moteurs d'Aviation "SNECMA", Paris, France

[21] Appl. No.: 523,959

[22] Filed: Sep. 6, 1995

Related U.S. Application Data

[62] Division of Ser. No. 326,386, Oct. 20, 1994.

[30] Foreign Application Priority Data

Oct. 20, 1993 [FR] France ................................. 93 12486

[51] Int. Cl.⁶ ................................................. G01N 21/64
[52] U.S. Cl. ..................................... 250/461.1; 250/458.1
[58] Field of Search ........................... 250/458.1, 459.1, 250/461.1; 356/333

[56] References Cited

U.S. PATENT DOCUMENTS

| | | | |
|---|---|---|---|
| 4,037,961 | 7/1977 | Macemon | 250/458.1 X |
| 4,194,217 | 3/1980 | van der Bosch | 356/323 X |
| 4,647,199 | 3/1987 | Ferber et al. | 20/461.1 X |
| 4,697,924 | 10/1987 | Akiyama | 356/333 |
| 5,001,353 | 3/1991 | Odake et al. | 250/461.1 |
| 5,303,026 | 4/1994 | Strobl et al. | 250/458.1 X |

FOREIGN PATENT DOCUMENTS 57-69221  4/1982  Japan ................................... 356/333

*Primary Examiner*—Carolyn E. Fields
*Assistant Examiner*—Edward J. Glick
*Attorney, Agent, or Firm*—Oblon, Spivak, McClelland, Maier & Neustadt, P.C.

[57] ABSTRACT

An apparatus for characterizing an analysis method based on fluorescent crack detection. The surface defects in articles to be checked are revealed by using a visible radiation around an excitation wavelength. The apparatus includes an illumination device, a camera and an image processor. The illumination device includes an ultraviolet light source, a monochromator and a light guide to focus the ultraviolet radiation.

6 Claims, 4 Drawing Sheets

PROCESS AND APPARATUS FOR AUTOMATICALLY CHARACTERISING, OPTIMISING AND CHECKING A CRACK DETECTION ANALYSIS METHOD

This is a division of application Ser. No. 08/326,386 filed on Oct. 20, 1994.

BACKGROUND OF THE INVENTION

1. Field of the Invention

The invention relates to a process and apparatus for optimizing, characterizing and checking a crack detection analysis method.

The invention is applicable to the detection of surface defects in all kinds of articles by the crack detection method, and more particularly to the automation, characterization and optimization of crack detection methods.

2. Summary of the Prior Art

In the known examination methods using crack detection the article to be examined is first prepared so as to reveal the surface defects. The preparation consists of applying to the surface of the article a penetrating composition, also called an indicator product, which contains a fluorescent or colored dye and which penetrates into the openings of the defects on the article surface, then removing the excess penetrating composition from the surface before applying a developing composition. The developing composition acts as a blotting paper and works by capillary action to attract the penetrating liquid composition containing the fluorescent dye out of the surface defects. The article is then exposed to appropriate lighting conditions such as an invisible fluorescent-producing light, and the presence of the surface defects is revealed by the emission of a visible fluorescent light by the dye of the penetrating composition remaining in the cracks after the removal of the composition from the article surface. As a rule, the penetrating composition contains fluorescent pigments which, when exposed to light in the ultraviolet range, re-emit a visible light usually disposed in the green-yellow color range. In this case the method is called the fluorescent crack detection method.

These methods of displaying defects provide a convenient way for checkers to examine articles visually. This visual evaluation is a difficult job and is very tiring for the eyes of the checking personnel, especially when articles produced in large series have to be checked, which affects concentration. Also, it is difficult to eliminate subjective influences from visual judgements.

Automatic examination of the indicators given by crack detection methods has also been proposed. For this purpose, it is known to use for the automatic collection and evaluation of defect indications opto-electronic systems comprising means for illuminating an image field in which the article to be checked is placed, video means such as a camera for obtaining digital images of the article, and image-processing means such as a computer for detecting possible surface defects in the article by comparison with images of reference articles.

However, the sensitivity and discrimination of the known automatic methods are usually limited by a number of factors, in particular the lighting conditions of the article to be checked and the pre-check preparation conditions of the article.

In the case of fluorescent crack detection methods illumination is provided by a light source which emits ultraviolet radiation. The radiation from the light source is filtered by filters to select a range of wavelengths appropriate to the particular penetrating composition chosen. Filters are also provided at the entry to the camera to eliminate parasitic radiations not originating from the penetrating composition. The use of these filters is not entirely satisfactory since they consume energy and increase the size of the automatic checking apparatus. Also, the filters do not have a pass band adapted to this kind of use and, in particular, it is very difficult to eliminate parasitic wavelengths around 400 nanometers. These wavelengths, which are disposed at the limit of the visible spectrum, usually have a very high energy. They pollute the images by causing reflections and affect the reliability of the checking result by masking crack information and causing parasitic indications called phantom defects.

Also, the known automatic methods are usually based on comparison with reference images or articles and give only qualitative results of uncertain reliability since they depend upon numerous parameters determined empirically by the user.

Checking reliability depends inter alia upon the article-preparing process preceding examination of the article, and in particular upon the choice of penetrating composition and upon the conditions in which the article is cleaned to remove excess penetrating composition. The reliability of the result also depends upon the camera and upon the processing of the images obtained by the video means.

SUMMARY OF THE INVENTION

It is an object of this invention to obviate the disadvantages of the known crack detection analysis methods, particularly fluorescent crack detection analysis methods, and to increase the reliability of the checking of articles by such methods.

To this end the invention aims to provide an automatic process and apparatus for quantitatively characterizing the known crack detection analysis methods, comparing such methods with one another, optimizing the various parameters affecting the reliability of the end result, and periodically checking the previously optimized analysis method to ensure that it has not undergone substantial drifting.

According to the invention, the quantitative characterization of a crack detection analysis method resides in determining the detection sensitivity and background noise produced by the analysis method by means of a processing of images obtained from one or more control specimens prepared by the method and subjected to appropriate and optimized illumination conditions.

The crack detection analysis method is optimized by searching for the influential parameters and for the value of these parameters which maximizes detection sensitivity and minimizes background noise.

The previously optimized analysis method is checked using the same control specimens to periodically verify that the detection sensitivity and the background noise have not worsened. If they have a warning signal indicates the malfunctioning and the cause is investigated.

The automatic apparatus comprises an illumination device adapted and optimized for fluorescent crack detection, wherein illumination of the article is effected by means of an ultraviolet light source, and is optimized by selecting a wavelength band centred on the spectrum line exciting the indicator product, this wavelength band being narrow enough to eliminate wavelengths emitted by the light source in the visible spectrum, and in particular the wavelength in the blue range around 400 nanometers.

More particularly, the invention provides a process for automatically characterizing, optimizing and checking a crack detection analysis method, comprising the steps of:

selecting at least one control specimen;

preparing said control specimen using an indicator product which reveals surface defects as in said analysis method;

exposing said control specimens to illumination suited to said indicator product used in said preparation step;

obtaining at least one image of said control specimens; and processing said at least one image to eliminate artifacts and determine the detection sensitivity and background noise produced by said analysis method.

The invention also provides an automatic apparatus for characterizing, optimizing and checking an analysis method based on fluorescent crack detection comprising an illumination device, a camera, and an image processor, said illumination device including, in series, a source of ultraviolet light, a monochromator for selecting a wavelength band centred around said excitation wavelength for said indicator product, and a light guide for focusing the ultraviolet radiation on a zone of the article to be checked.

Other features and advantages of the invention will become apparent from the following description of embodiments thereof, given by way of non-limiting example, with reference to the accompanying drawings.

DESCRIPTION OF THE PREFERRED EMBODIMENTS

In crack detection examination of articles the articles are prepared by using indicator products giving a very high contrast between crack indication and the article surface. In the case of fluorescent crack detection the indicator products are fluorescent pigments which fluoresce strongly in ultraviolet light, the surface background remaining dark. The resulting contrast can be used for automatic checking of the article by recording the brightness of the fluorescent indications by means of an appropriate photosensitive device and by processing the data thus obtained.

Figure 1:
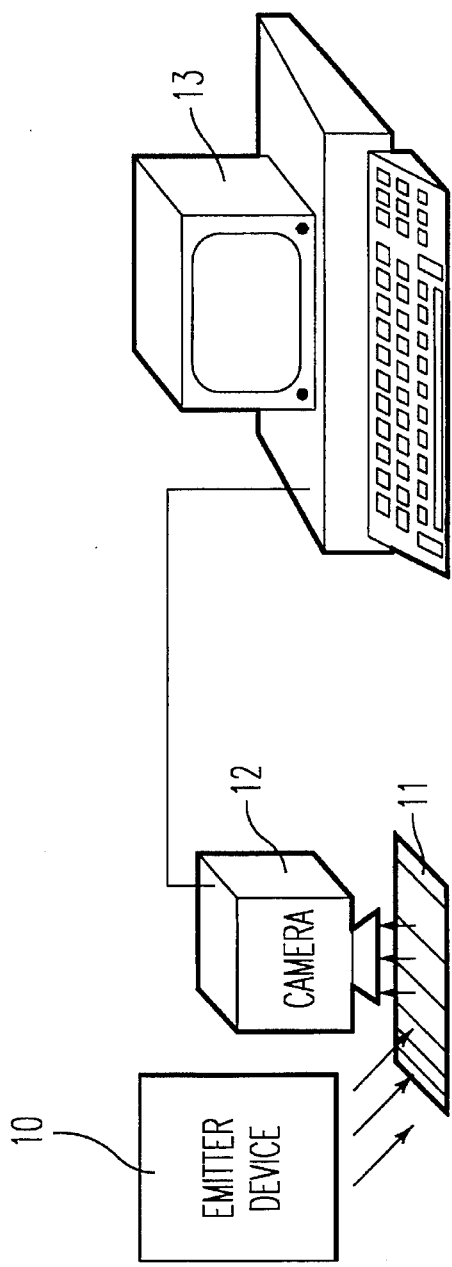
FIG. 1 shows diagrammatically apparatus for obtaining and processing images in accordance with the invention.

FIG. 1 shows apparatus in accordance with the invention for obtaining and processing images. The apparatus comprises a light emitter device 10, also called an illumination device, for illuminating an image field in which the article 11 to be checked is disposed. The article is then observed optically and processed electronically by a television camera 12 which is very sensitive to a low light level, and the resulting image is processed by an image processing system 13, for example a computer.

Figure 2:
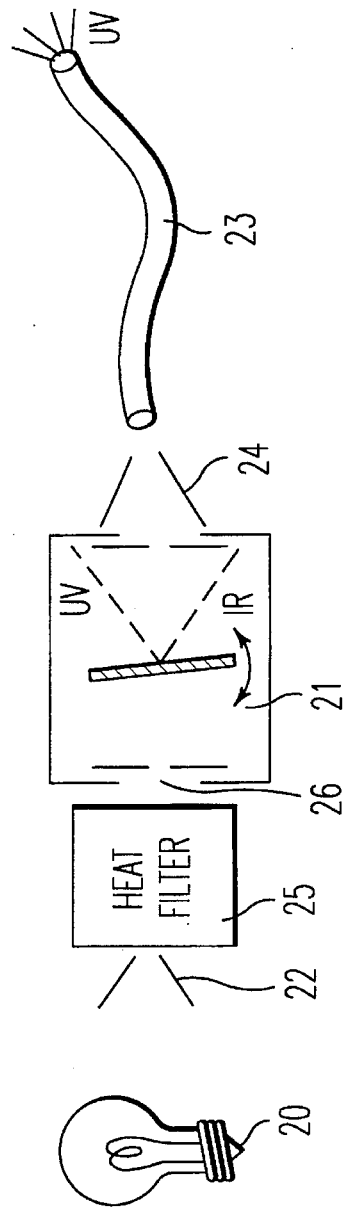
FIG. 2 shows diagrammatically one embodiment of a device for illuminating articles checked by fluorescent crack detection in accordance with the invention.

FIG. 2 shows an embodiment of an illumination device for articles to be checked by fluorescent crack detection. This device 10 comprises a light source 20 chosen according to the indicator product used during the article preparation cycle. As an example, the indicator product may be of the kind which re-emits visible radiation whose wavelength is in the yellow-green color range between 450 and 550 nanometers when excited by nearby ultraviolet radiation centred on a wavelength of the order of 365 nanometers. The ultraviolet light source may be a laser or a multispectrum lamp such as a mercury vapour lamp. Preferably, when such a lamp is used it is of the variable power kind so as to maintain a constant illumination. Another way of adjusting the illumination is by shifting the spectrum of emitted wavelengths.

The radiation from the light source is transmitted through a monochromator 21 comprising at least one dispersive grating and by way of a first optical matching and focusing device 22. The monochromator output signal is directed through a second optical matching and focusing device 24 to a light guide 23. The function of the focusing devices 22, 24 is to focus all the emitted power on the monochromator entry slot and into the interior of the light guide.

To obtain a high-contrast crack indication the monochromator 21 is used as an emission filter and is adapted to meet two main constraints—first, the selected wavelength band around the spectrum excitation line of the indicator product, for example, 365 nanometers, must not be too narrow to emit sufficient energy, and second, it must be selective enough to eliminate wavelengths emitted by the light source in the visible spectrum, more particularly the wavelengths in the blue range around 400 nanometers when a mercury vapour lamp is used. By way of example these two constraints can be met by using a short focal length double monochromator comprising two mechanically coupled dispersive gratings adapted to select the same wavelength. To prevent the two gratings from being damaged by the heat from the lamp 20 they can be hardened chemically in advance by a surface treatment. Also, a heat filter 25 can be placed upstream of the monochromator 21 between the first focusing device 22 and the monochromator inlet 26 to limit the heat at the monochromator inlet. The heat filter may be, for example, a system comprising double quartz walls separated by a vacuum. Cooling is then effected by natural convection or by circulation of a fluid.

The light guide must transmit ultraviolet radiation faithfully with very little attenuation and without producing a parasitic radiation. A liquid guide is preferred for its flexibility and ruggedness; but an optical fibre, for example, of silica, may be used although this kind of fibre is very fragile.

The light guide 23 has an optical focusing system (not shown), such as quartz windows, at each end in order to produce homogeneous illumination and focus the ultraviolet radiation on a small zone of the article, measuring 25 mm ×25 mm for example.

Small zones of the article surface are examined in succession by moving either the article or the complete system—i.e., the camera and the illumination device-manually or automatically.

In order to characterize a fluorescent crack detection analysis method the process consists of determining the detection sensitivity and background noise produced by the method. To this end, the crack detection analysis method is applied to one or more control specimens having surface cracks.

To evaluate detection sensitivity it is particularly convenient to select as control specimens standard blocks which have cracks of known depth and which have a good surface condition. For example, brass blocks covered with a chromium-nickel deposit of a predetermined thickness and having cracks whose depth is equal to the thickness of the chromium-nickel deposit are commercially available. Blocks are available with various chromium nickel deposit thicknesses between 5 and 100 micrometers. The use of these blocks as control specimens enables the detection sensitivity of the process to be evaluated.

To evaluate background noise the control specimens selected must be representative of the articles to be checked so far as material and the surface condition are concerned. The specimens can be selected from among the articles to be checked or from pieces of articles or can be test pieces representative of the material and surface condition of the articles to be checked.

Each control specimen is prepared beforehand to reveal surface defects by means of a penetrating composition. It is then subjected to ultraviolet radiation from an illumination device, such as the one described with reference to FIG. 2. The illumination device is adjusted so that the illumination intensity is as constant and homogeneous as possible in order to obtain good quality images which are comparable with one another. Visible radiation emitted by the control specimen is detected and is converted into a video image by means of a video camera to form a coded digital image having a dynamic range of, for example, 256 grey levels. Preferably, the camera is adjusted to produce a background grey level near zero. The sensitivity of the camera used depends upon the depth of the cracks to be analysed, the sensitivity of the penetrating agent used and the required accuracy of the result. Camera magnification is adjusted so as always to cover the same image field; for example, in the case of brass blocks covered by a chromium nickel deposit camera magnification is adjusted so that the cracks take up the full height of the image. The images are always integrated the same number of times, for example 256 times, in order to suppress noise. The images are processed by an image processing facility for extraction of detection sensitivity and background noise.

Figure 3:
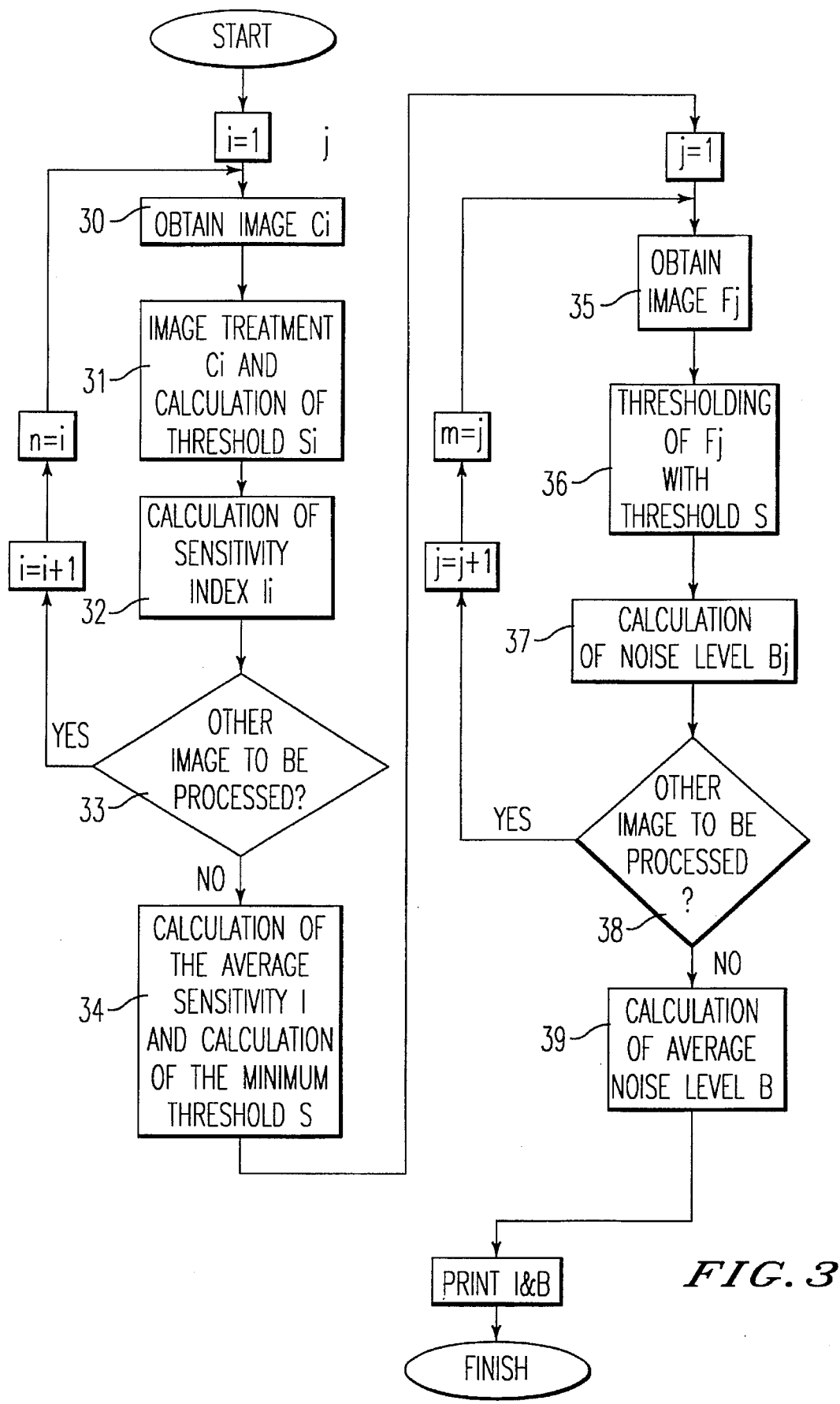
FIG. 3 shows a flow chart of various stages in the image processing in one embodiment of the process according to the invention.

FIG. 3 shows, in the form of a sequence of function blocks, the various stages of the image processing in the process according to the invention. The processing involves two phases. In a first phase, corresponding to stages 30 to 34, images Ci are obtained in stage 30 from control specimens, for example standard blocks, and then processed in order to derive, in stage 31, a threshold value Si for binarizing the image in order to eliminate artifacts, and in stage 32 a sensitivity index Ii. This processing is described in more detail with reference to FIG. 4. Stage 33 is a test for determining whether there are further images Ci to be processed. If the test is positive the iteration index i and the number n of processed images are incremented and stages 30 to 32 are repeated with the next image. If the test is negative the average I of the sensitivity indices Ii obtained from each image Ci and the minimum threshold value S are calculated in stage 34.

In a second phase, corresponding to stages 35 to 39, images Fj are obtained in stage 35 from specimens in the form of articles or representative samples of articles to be checked. These images are thresholded in stage 36 against the minimum threshold value S obtained in the determination of the average sensitivity index I in phase one, and are then processed in stage 37 to derive the noise level Bj. The stage 38 is a test for determining whether there are further images Fj to be processed. If the test is positive the iteration index j and the number m of processed images are incremented and stages 35 to 38 are repeated with the next image. If the test is negative the average B of the noise level Bj obtained for each image Fj is calculated in stage 39 and the process is terminated. The values I and B denote respectively the detection sensitivity and the background noise produced by the crack detection analysis method under consideration.

Figure 4:
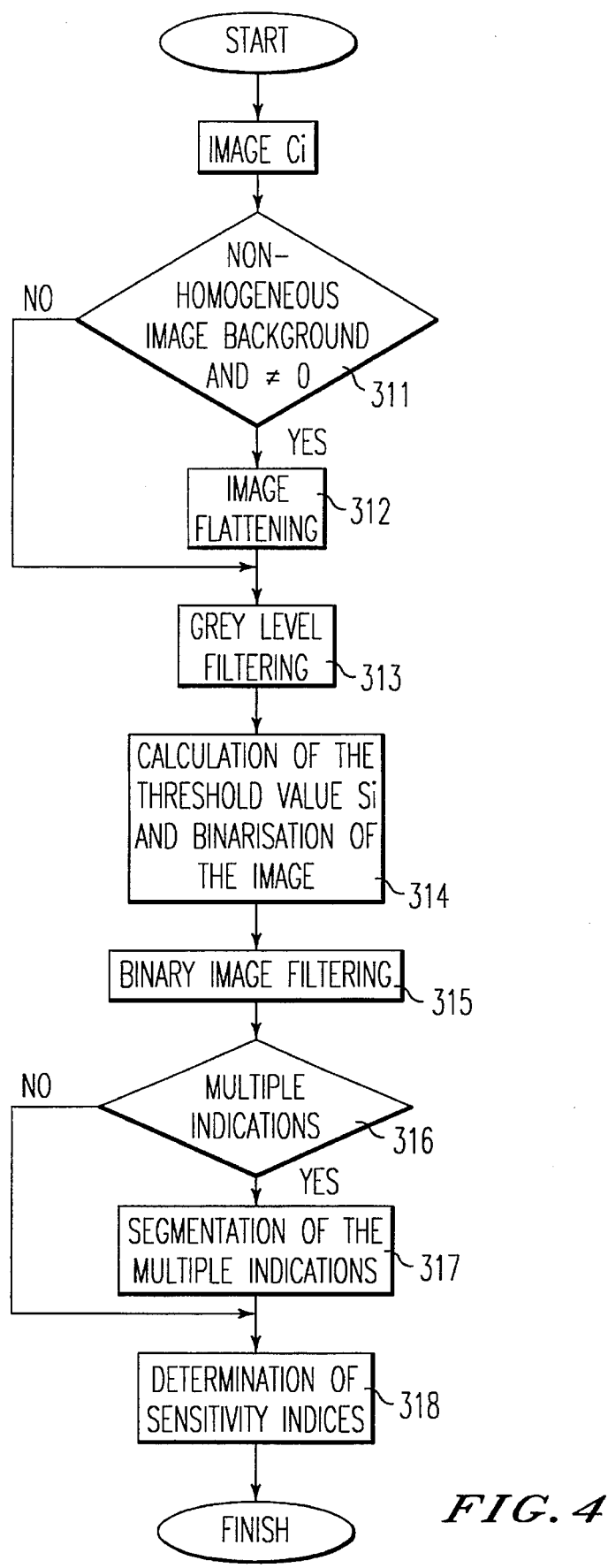
FIG. 4 shows a flow chart of substages for determining a sensitivity index in the image processing sequence shown in FIG. 3.

FIG. 4 shows, in the form of function blocks, substages of the method of processing the images Ci to determine the sensitivity index. For the images to be comparable with one another, the background must be homogeneous and be of approximately the same value for all the images Ci.

The first stage 311 of the processing consists of checking each image to verify that the image background is homogeneous and corresponds to a given grey level, for example approximately from 0 to 5 grey levels. If the background is not homogeneous and/or near zero, stage 312 effects a reflattening of the image involving removal of the background indications. This operation can be performed by various methods such as, for example, by obtaining a white image and substracting it from the image Ci. Another possibility is to remove the background indications by correcting the image relative to itself by means of morphological or frequency filterings or by correcting the image relative to a reference image. If the background is homogeneous a grey level filtering of the image is effected in stage 313. This filtering serves to combine discontinuous indications corresponding to a single crack. To be combined the discontinuous indications must be close enough together to appear continuous to the naked eye. The filtering can be performed with the use of mathematical morphology filters or frequency filters.

The stage 314 calculates the threshold value Si for binarizing the image in order to remove artifacts therefrom. The threshold value is chosen to be twice the average luminance value of the luminance maxima.

The factor two corresponds to a mid-height evaluation of the relevance of a luminance peak. The luminance maxima are obtained after the binarization operations on the image with an approximate threshold value obtained from the histogram of the image and chosen equal to the sum of the average value and standard deviation of the image luminances, from skeletonization of the binarized image and from multiplication of the skeletonized binary by the grey level image.

The image is then binarized at this threshold value to remove from the image all points whose luminance value is less than the threshold value. A second filtering of the binary image is effected in stage 315 in order to eliminate minor artifacts not eliminated in the stage 313 during the grey level filtering of the image. The second filtering comprises linear expansion and linear erosion operations.

In the next stage 316 a test searching for multiple indications is carried out to detect cases in which two cracks very close together have joined together to form just a single crack. To this end, the filtered binary image is skeletonized in order to find the triple points which have three neighbours. If the test is positive the multiple indications are segmented in stage 317. Segmentation resides in separating out merged crack indications. Since the triple points are usually remote from the points at the ends, segmentation is effected after a search has been made for the end points and after a proximity test has been made between the triple points and the end points.

When all the multiple indications have been separated, the various parameters for determining a sensitivity index are calculated in stage 318. The sensitivity index is chosen, for example, to be equal to the product of the length index by the resolution index. The length index is equal to the ratio of the read-off length to the theoretical length of the indications, and the resolution index is equal to the ratio of the average luminance of the luminance maxima to the read-off width of the indications.

The theoretical length of a crack is known and corresponds to the height of the image when the specimens are positioned so that the cracks appear vertical in the image. The number of cracks in a given specimen is determined by previous observations thereof with binoculars. The width of the indications is obtained by calculating the ratio between the area occupied by the prints whose luminance is above the first threshold value and the read-off length of the indications.

The detection sensitivity and background noise thus determined for a given fluorescent crack detection analysis method by the process in accordance with the invention enable the method to be characterized quantitatively.

In addition, the process in accordance with the invention can be used to optimize the influential parameters by searching for those values thereof which maximize detection sensitivity and minimize background noise. Optimization of a given analysis method therefore consists of selecting the influential parameters, searching for those values thereof which maximize detection sensitivity and verifying that these parameter values do not increase background noise.

Figure 5:
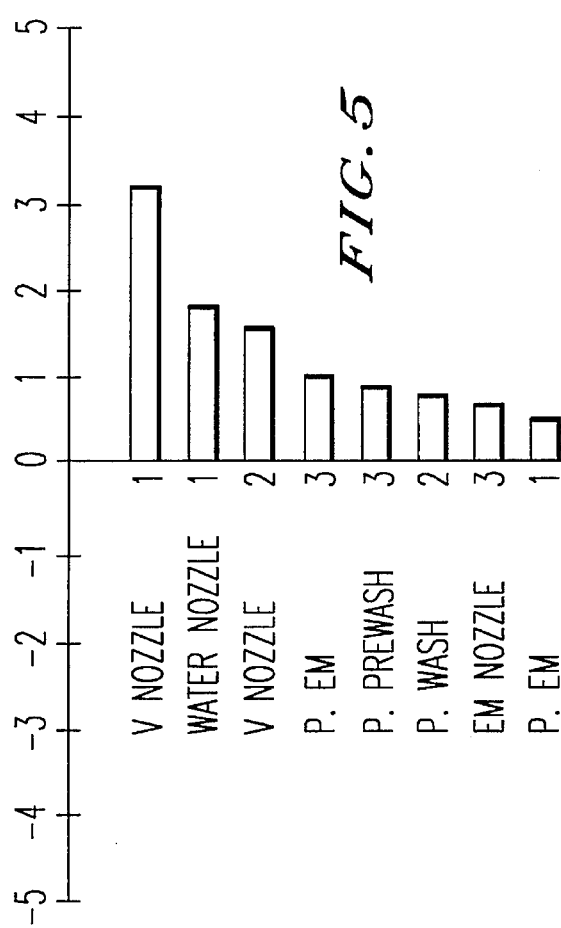
FIG. 5 is a plot illustrating an example of the effects of various parameters on detection sensitivity for a given fluorescent crack detection analysis method.

FIG. 5 shows one example of the effect of various parameters on detection sensitivity for a given fluorescent crack detection analysis method. The results were obtained from standard blocks. The change in sensitivity is visualized in FIG. 5 by six different parameters each taking three different values numbered 1 to 3.

The six parameters are:

the speed at which the nozzle is moved (V NOZZLE) during washing the articles relatively to the number of passes made by the nozzle over the articles to be washed. Three different nozzle speeds are envisaged, the number of nozzle passes being greater as nozzle speed is greater so as to maintain a constant ratio. In FIG. 5 speed No. 1 is less than speed No. 2 which, in turn, is less than speed No. 3;

the type of water nozzle (WATER NOZZLE) used to wash the article;

the pressure (P.EM) of the emulsifier applied to the articles;

the pressure (P. prewash) of the water for prewashing the articles;

the pressure (P. wash) of the water for washing the articles; and the kind of nozzle (EM NOZZLE) used to apply the emulsifier to the articles.

In FIG. 5 the effects of each parameter on detection sensitivity are measured relative to the average value of each parameter, the parameters being arranged in an order making it possible to visualize the best values for optimizing detection sensitivity. Thus, this sensitivity is better when the speed of the washing nozzle is low, the washing nozzle used is nozzle No. 1, and the pressure of the water for prewashing and washing the articles corresponds to the third value considered.

Figure 6:
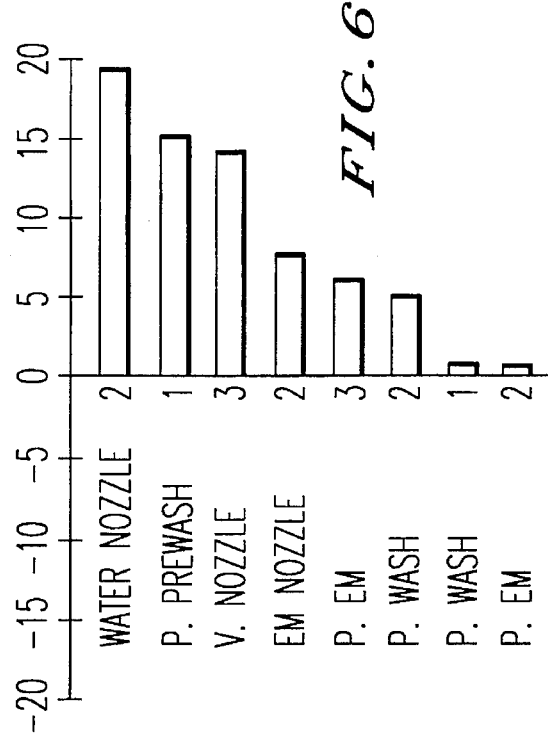
FIG. 6 is a plot illustrating an example of the effect of said various parameters on the background noise produced by a given fluorescent crack detection analysis method.

FIG. 6 shows an example of the effects of various parameters on the background noise of a given fluorescent crack detection analysis method. The analysis method and the parameters considered are the same as for FIG. 5, and the results were obtained from a testpiece representative of the articles to be checked.

The effects of each parameter on background noise are measured relative to the average value of each parameter. Thus, FIG. 6 verifies that the choice of washing nozzle speed not only helps to maximize detection sensitivity but also to minimize background noise. This parameter value can therefore optimize the chosen analysis method.

Finally, when the analysis method has been characterized and optimized, the process in accordance with the invention can also be used to check periodically that the analysis method has not drifted. To this end the detection sensitivity and background noise values produced by the analysis method are periodically verified from the same control specimens as were used for initially characterizing the analysis method. If the results have deteriorated, the causes for the malfunctioning of the analysis method are investigated with a view to remedying them.

If will of course be appreciated that the invention is not limited to the embodiment just described. In particular the method of processing images to determine the detection sensitivity and background noise is not limited to fluorescent crack detection but is applicable to any crack detection analysis method.

We claim:

1. Apparatus for automatically characterizing, optimizing and checking an analysis method based on fluorescent crack detection wherein articles to be checked have surface defects revealed by the use of an indicator product which emits a visible radiation under illumination centred around an excitation wavelength for said indicator product, said apparatus comprising an illumination device, a camera, and an image processor, said illumination device including, in series, a source of ultraviolet light, a monochromator for selecting a wavelength band centered around said excitation wavelength for said indicator product, and a light guide for focusing the ultraviolet radiation on a zone of the article to be checked.

2. Apparatus according to claim 1, wherein said illumination device also comprises two focusing devices, one disposed at the entry of said monochromator and the other disposed at the exit therefrom.

3. Apparatus according to claim 2, wherein said illumination device further comprises a heat filter upstream of said monochromator.

4. Apparatus according to claim 1, wherein said monochromator is a double monochromator comprising two mechanically coupled dispersive gratings adjusted to select the same wavelength.

5. Apparatus according to claim 1, wherein said camera produces at least one image of said article to be checked and wherein said image processor processes said image to eliminate artifacts and determine the detection sensitivity and background noise produced by said analysis method.

6. Apparatus according to claim 5, wherein said image processor corrects said image in order to obtain a homogeneous background having a predetermined grey level, filtering the corrected grey level image to combine discontinuous indications, calculating a threshold value and binarizing the corrected and filtered image at said threshold value in order to retain only those points of the image which are likely to correspond to a defect in the article, filtering the binary image in order to eliminate image points which are not associated with defects and have not been eliminated by said filtering of said corrected grey level image, searching for multiple indications in order to detect close-together defects which have merged, separating said indications of merged defects and determining a sensitivity index.

* * * * *